(12) United States Patent
Suijver et al.

(10) Patent No.: US 8,040,612 B2
(45) Date of Patent: Oct. 18, 2011

(54) FLUID LENS WITH PRESSURE RELEASE SYSTEM

(75) Inventors: Jan Frederik Suijver, Eindhoven (NL); Stein Kuiper, Eindhoven (NL); Bernardus Hendrikus Wilhelmus Hendriks, Eindhoven (NL); Szabolcs Deladi, Eindhoven (NL); Antonius Johannes Josephus Rademakers, Eindhoven (NL); Cornelius Antonius Micolaas Maria Van Der Vleuten, Eindhoven (NL); Johannes Wilhelmus Weekamp, Eindhoven (NL); Waltherus Cornelis Jozef Bierhoff, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/811,831

(22) PCT Filed: Jan. 12, 2009

(86) PCT No.: PCT/IB2009/050098
§ 371 (c)(1),
(2), (4) Date: Jul. 7, 2010

(87) PCT Pub. No.: WO2009/090585
PCT Pub. Date: Jul. 23, 2009

(65) Prior Publication Data
US 2010/0277809 A1 Nov. 4, 2010

(30) Foreign Application Priority Data
Jan. 14, 2008 (EP) ...................................... 08150230

(51) Int. Cl.
*G02B 1/06* (2006.01)
*G02B 3/12* (2006.01)

(52) U.S. Cl. ........................................ 359/665; 359/666
(58) Field of Classification Search .................. 359/665, 359/666
See application file for complete search history.

(56) References Cited

U.S. PATENT DOCUMENTS

| 3,765,403 | A | 10/1973 | Brenden |
| 6,188,526 | B1 | 2/2001 | Sasaya et al. |
| 7,499,223 | B2 * | 3/2009 | Berge et al. .................. 359/666 |

FOREIGN PATENT DOCUMENTS

| EP | 1736802 A2 | 12/2006 |
| EP | 1780575 A1 | 5/2007 |
| EP | 1804109 A1 | 7/2007 |
| JP | 2002162506 | 6/2002 |
| WO | 2004099847 A1 | 11/2004 |
| WO | 2005093489 A2 | 10/2005 |

* cited by examiner

*Primary Examiner* — William Choi

(57) ABSTRACT

Fluid lens system includes a container enclosing a fluid arranged to refract incoming waves. A pressure release mechanism is in contact with the fluid so as to compensate changes in its volume due to thermal variations. The pressure release mechanism is positioned within a pathway of incoming waves. The fluid container may be connected via a tube to the fluid as a reservoir which is arranged within or outside the container, such as beyond an image sensor. Alternatively, an easily compressible body such as a small closed metal bellows enclosing a gas, is positioned inside the fluid to absorb volume changes by compression. The container may have an inner container part that fits inside an outer container part, where the pressure release mechanism is positioned within the outer container part. A fluid filled cavity including a compressible body may be formed between the inner and outer container parts.

29 Claims, 3 Drawing Sheets

FLUID LENS WITH PRESSURE RELEASE SYSTEM

FIELD OF THE INVENTION

The invention relates to the field of fluid lenses, such as fluid lenses for medical applications. More specifically, the invention relates to the field of fluid lenses suited for large thermal variations.

BACKGROUND OF THE INVENTION

Fluid type lenses, or liquid lenses, have a number of well known properties that make such lenses suitable for medical applications, e.g. for invasive medical instruments for imaging or treatment. For applications requiring high quality performance of the lens, the fluid is often enclosed in a rigid container. However, when exposed to large thermal variations, e.g. the heating of up to or more than 100° C. as required for disinfection of medical instruments, such lenses suffer from the fact that the pressure inside the lens increases due to thermal volume expansion of the fluid. E.g. a water lens with a diameter of 2 mm and a thickness of 1 mm will expand its thickness by about 0.01 mm when exposed to a temperature rise of 50° C. These effects can lead to permanent damage of the lens which therefore in practice excludes such lenses for use more than once.

EP 1 736 802 A2 describes a liquid lens in which internal pressure in the lens due to thermal expansion is remedied by introducing a volume of gas in contact with the liquid of the lens. The gas will then be compressed during high temperature, thus serving to limit the pressure in the fluid lens. However, this solution has the disadvantage that over time the gas molecules will distribute throughout the lens due to diffusion into the fluids that complies the lens. Further, it is a disadvantage of the mentioned lens that the gas container is positioned projecting outward in a radial direction thus increasing the total size of the lens in a dimension perpendicular to the paths of light through the lens.

WO 2004/099847 describes a liquid lens with expansible joints arranged in connection with one transparent end of the container enclosing the liquid. Hereby the transparent end can move, thereby increasing the container volume and thus releasing the pressure inside the lens caused by thermal variation. A disadvantage of such lenses is that optical quality is compromised, because the expansible joints will to some extent allow the transparent window of the lens to tilt compared to the rest of the lens, thereby influencing the optical properties of the lens.

SUMMARY OF THE INVENTION

According to the above explanation, it is an object of the present invention to provide a fluid lens capable of withstanding high thermal variations without permanent damage. Still, the fluid lens should have compact dimensions so as to allow invasive medical applications where only a limited space is available, especially with respect to ensure a small diameter.

In a first aspect, the invention provides a lens system including a fluid lens including a container enclosing a first fluid, e.g. also a second fluid, arranged to refract incoming waves, and a pressure release mechanism arranged in contact, such as direct contact, with the first fluid of the fluid lens so as to compensate changes in volume of the first fluid due to thermal variations, wherein the pressure release mechanism is positioned within a pathway of incoming waves.

Such a lens system is suited for applications where the fluid lens is subject to large thermal variations, such as the use in medical devices, where a cleaning procedure in some cases includes autoclaving which means exposing the device to a temperature of 135° C. for 10 minutes. With the lens system according to the first aspect, it is possible to withstand such exposure without any permanent damage due to the pressure release mechanism. Even though the pressure release mechanism is only applied directly to the first fluid, typical lenses include also a second fluid interfacing the first fluid. In such embodiments, the pressure release of the first fluid will be enough to ensure pressure release of the entire lens, since the interface between the first and second fluids will ensure that the total volume change of the two fluids will be released even though only one of the fluids has a pressure release mechanism.

By 'pathway of incoming waves' is understood a space with a cross section defined by the area where incoming waves can enter the fluid lens, and in principle with infinite extension in a direction of incoming waves or rays to the fluid lens. In a three dimensional lens system, a body is defined by the outermost marginal rays, i.e. the rays/waves that travel furthest from the principal ray defining the center of the optical/acoustical path of the lens. This body, cylindrical in shape for a cylindrically symmetric lens, determines a spatial limitation. At a certain position along the rays' paths, a cross-section of this outermost body of marginal rays will have a maximal diameter. A body of that maximal diameter centered around the principal ray, extended to plus and minus infinity in the ends, is understood as the pathway of incoming waves. a total volume. Since the actual optical/acoustical path through the lens in practice occupies less space than this pathway of incoming waves, there is still space available for the pressure release mechanism within the pathway of incoming waves without disturbing waves passing through the lens. A sketch illustrating the pathway of incoming waves is seen in FIG. 1.

In spite the presence of the pressure release mechanism, the lens can be formed very compact, especially without compromising a small diameter which is critical parameter for medical applications within the invasive field. This is due to the position of the pressure release mechanism within the pathway of incoming waves, thus the presence of the pressure release mechanism does not require larger dimensions of the lens. The invention is based on the insight that normally due to the refraction, the entire pathway of incoming waves will not be fully occupied by waves, and thus there are parts of the pathway that can be used for the pressure release mechanism without disturbing incoming waves, and thus without compromising performance of the lens.

Due to the position of the pressure release mechanism within the pathway of incoming waves, the total outer diameter of the lens system including the pressure release mechanism is not increased due to the presence of the pressure release mechanism. In other words, almost the entire total outer diameter of the lens system is available for the fluid lens in the lens system according to the first aspect. Thus, the lens system is suited for medical applications such as endoscopes, catheters and needles for imaging or treatment, e.g. using ultrasonic waves.

In some embodiments, the pressure release mechanism is positioned in a peripheral part of the pathway of incoming waves, such as the pressure release mechanism being positioned outside a central part of the pathway of incoming waves so as to avoid affecting refraction properties of the fluid lens. Hereby it is possible to provide a high tolerance to thermal changes of the fluid lens and still maintain a high quality of the lens, since the pressure release mechanism can be positioned out of the way of typically incoming waves.

The pressure release mechanism can be positioned at various positions. The pressure release mechanism may be positioned outside the container, such as before or after the fluid lens, seen in a direction of the incoming waves.

Especially, the lens system may include an image sensor arranged to sense waves after refraction in the fluid lens, and in such embodiments the pressure release mechanism can be positioned beyond the sensor, seen in a direction of the incoming waves. Still, the pressure release mechanism, e.g. a container connected to the first fluid by a tube positioned in a peripheral part of the lens, is within the pathway of incoming waves, but positioned outside the range of the incoming waves, thus allowing a rather uncritical positioning of the pressure release mechanism.

The pressure release mechanism may alternatively be positioned inside the container, such as:
1) inside the container but outside the first fluid, e.g. inside a second fluid, or
2) inside the first fluid, i.e. with the pressure release mechanism being totally or at least partially encircled by the first fluid.

For embodiments according to 2), the pressure release mechanism may include a compressible container enclosing a compressible medium, such as a bellows enclosing a gas. By a bellows is understood a compressible container, e.g. shaped such that it allows a large degree of compression even though the bellows is formed by a material with a rather low elasticity. Especially, such bellows may be a metal bellows which can withstand high temperatures. In a preferred embodiment, the bellows is a ring shaped bellows positioned in the first fluid in a peripheral part of the pathway of incoming waves. Such ring shaped bellows allows incoming rays to pass a central part of the lens, i.e. inside the ring shaped bellows, and thus the bellows will not disturb the quality of the lens system.

For all mentioned embodiments where the pressure release mechanism is positioned outside the first fluid, the pressure release mechanism preferably is a pressure release container connected to the first fluid via a tube so as to accommodate changes in volume of the first fluid due to thermal variations. The pressure release container will take up some space in order to be able to accommodate the required volume of the first fluid in case a large thermal variation should be covered. Therefore, the pressure release container should be carefully positioned within the pathway of incoming waves. The tube connecting the pressure release container and the first fluid can be very thin, e.g. with an outer diameter of 0.5 mm, and can thus easily be positioned in the lens system without any disturbing effect on the quality of the lens.

To reduce the space occupied by the pressure release mechanism in one of the mentioned positions in the lens system, it may be preferred to combine two or more of the above-mentioned pressure release mechanism positions. Hereby, the same volume change of the first fluid can be compensated with smaller components, e.g. by combining a first pressure release mechanism positioned within the first fluid, and a second pressure release mechanism positioned outside the container.

In preferred embodiments, the container is substantially rigid and has two opposing boundaries of a material being substantially transparent for incoming waves, e.g. glass in case the lens is suited for light. The container may have a cylindrical shape with the two opposing boundaries defining ends of the container. The container may alternatively to the cylindrical shape have four parallel sidewalls of rectangular shape thus forming a rectangular container with two opposing wave transparent boundaries defining ends of the container. More alternatively, the sidewalls may be non-parallel and form a part of a pyramid.

The pressure release mechanism may be positioned within a space defined by extension of the sidewalls of the container, i.e. including the space beyond end boundaries of the container. Hereby the pressure release mechanism does not occupy space requiring a larger outer periphery than the container itself. This is advantageous for medical applications where the lens needs to be inserted in narrow ducts.

In preferred embodiments, the fluid lens includes a second fluid different from the first fluid, and wherein the second fluid is arranged with an interface to the first fluid so as to refract incoming waves at the interface. The first fluid is preferably a liquid, such as water or an oil. The second fluid may also be water or an oil. The two fluids should be immiscible, and one of the fluids should be electrically conductive while the other is not. As mentioned, such lens embodiments can be pressure released with only one pressure release mechanism, but it may be preferred to have separate pressure release mechanisms on both fluids.

In preferred embodiment, the fluid lens is arranged to refract ultrasonic waves or light waves.

The lens system may include a second fluid focus lens including a second pressure release mechanism. E.g. such embodiment may be a zoom lens system for an endoscope or the like.

Preferably, all single components of the lens system are made from materials that can withstand autoclaving, i.e. 135° C. without permanent damage.

In a second aspect, the invention provides a medical device including a lens system according to the first aspect. The lens system is preferably mounted in connection with a catheter, an endoscope, or a needle, especially invasive medical instruments. The lens system of such medical device may be used for imaging, e.g. ultrasonic imaging, or for medical treatment, such as for ultrasonic ablation.

It is appreciated that embodiments and advantages mentioned for the first aspect apply as well for the second aspect. Further, it is appreciated that the mentioned aspects and embodiments thereof may be combined in any way.

In a third aspect, the invention provides a lens system including
a fluid lens including a container enclosing a first fluid arranged to refract incoming waves, the container including an inner container part that fits inside an outer container part, wherein the inner container part is in rigid connection to at least a one boundary arranged for penetration of incoming waves, and
a pressure release mechanism positioned within the outer container part, and arranged in contact with the first fluid of the fluid lens so as to compensate changes in volume of the first fluid due to thermal variations.

As the lens system of the first aspect, the lens system of the third aspect is also suited for applications where small dimensions are required, e.g. medical applications, such as ultrasonic imaging or ultrasonic treatment, and where at the same time high temperature variations can occur, e.g. as mentioned during medical cleaning procedures. Even though the container enclosing the first fluid has inner and outer parts, it is possible to implement compact lens systems with a small outer diameter, as will be described in the following.

In one embodiment, the outer container part is arranged in rigid connection with a first boundary arranged for penetration of incoming waves, and the inner container part is in rigid connection with a second boundary arranged for penetration of incoming waves, and wherein the pressure release mechanism includes a flexible and fluid tight connection between the inner and outer container parts arranged to allow pressure release of the first fluid upon relative translation between the inner and outer container parts. In this embodiment the flexible and fluid tight connection between inner and outer container parts is used to allow the first fluid to expand and contract its volume which is then absorbed by relative movement between the inner and outer container parts.

Preferably, this relative movement is a one-dimensional translation so as to ensure en boundaries of the lens to remain parallel irrespective of the relative position between the inner and outer container parts, thereby ensuring high performance of the lens. Especially, the inner and outer container parts may have cylindrical shapes with different diameters such that the inner container part fits inside the outer container part with a minimal clearing arranged for the relative translation.

In a preferred embodiment, the inner container part further encloses a second fluid arranged with an interface to the first fluid for refraction of incoming waves.

In another embodiment, the first fluid is connected to a cavity formed between the inner and outer container parts, e.g. between inner and outer walls of the container, and wherein the pressure release mechanism includes a compressible container enclosing a compressible medium arranged in the first fluid inside this cavity so as to release pressure in the first fluid by compression of the compressible container. The cavity that may completely surround the inner container part results in an increase outer dimension of the lens, however in this embodiment moving parts of the container can be avoided, and thus end boundaries arranged for transmission of incoming waves can be mounted fixed, thus ensuring a high performance of the lens which is stable and insensitive to wear in moving parts. The compressible container may be a ring shaped bellows enclosing a gas, e.g. atmospheric air, nitrogen, or $CO_2$. Alternatively, several gas filled compressible containers, e.g. metal bellows, are positioned in the cavity. A preferred shape of the lens according to this embodiment is cylindrical, e.g. such that both inner and outer container parts form two concentric cylinders with the cavity being the space between the two cylinders, and wherein an opening in the inner cylinder provides contact between the first fluid and the cavity.

In a preferred embodiment, the inner container part together with the first fluid and a second boundary encloses a second fluid.

In a fourth aspect, the invention provides a medical device including a lens system according to the third aspect. The lens system is preferably mounted in connection with a catheter, an endoscope, or a needle, especially invasive medical instruments. The lens system of such medical device may be used for imaging, e.g. ultrasonic imaging, or for medical treatment, such as for ultrasonic ablation.

It is appreciated that features of the mentioned aspects can be intermixed.

BRIEF DESCRIPTION OF THE DRAWINGS

Embodiments of the invention will be described, by way of example only, with reference to the drawings, in which.

DETAILED DESCRIPTION OF EMBODIMENTS

Figure 1:
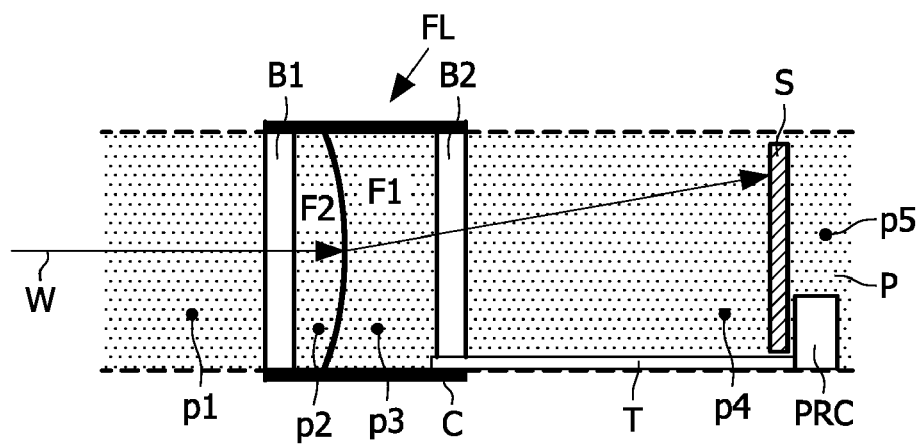
FIG. 1 illustrates different positions for the pressure release mechanism in relation to a fluid lens.

FIG. 1 illustrates one embodiment of the invention. A longitudinal section of a fluid lens FL with a rigid container C encloses a first fluid F1 and a second fluid F2. The container C has two opposing boundaries or windows B1, B2 which are transparent to incoming waves W, such as light waves or ultrasonic waves. The container C may be rectangular or circular in cross section. The lens refracts the incoming wave W at an interface between the first fluid F1 and an optional second fluid. The interface may have a controllable shape so as to allow adjustment of the fluid lens FL. The illustrated embodiment includes an image sensor S. After refraction in the fluid lens FL, the incoming wave W meets the image sensor S that can generate an electric signal in response to the sensed image.

The fluid lens FL defines a pathway P for incoming waves W, this pathway P such as optical pathway in case the waves W are light waves, being illustrated by the dotted area within the dashed lines. In the illustrated embodiment, this pathway P coincides with inner part of the sidewalls of the container C. According to the invention the lens system includes a pressure release mechanism which is connected to the first fluid F1. In the embodiment of FIG. 1, the pressure release mechanism includes a pressure release container PRC, either a rigid or compressible container, connected to the first fluid F1 via a tube T. As seen, the pressure release container PRC is positioned in the pathway of incoming waves, beyond the image sensor S, i.e. behind the image sensor S, seen in a direction of incoming waves W.

In FIG. 1 a total of five principally different positions p1, p2, p3, p4, p5 of the pressure release mechanism is illustrated, all within the pathway P. Position p1 is outside the container C, before the fluid lens FL, seen in the direction of incoming waves W. Position p2 is inside the container C, but outside the first fluid F1, namely inside the second fluid F2. Position p3 is inside the container C and inside the first fluid F1. Position p4 is outside the container C, after the container but before the image sensor S, seen in the direction of incoming waves W. Position p5 is outside the container C, after the image sensor, seen in the direction of incoming waves W, i.e. the position of the illustrated pressure release container PRC. Preferably, for all possible positions p1, p2, p3, p4, p5 of the pressure release mechanism, this mechanism is preferably positioned in a peripheral part of the pathway P, such that incoming waves W are not disturbed, or at least only minimally disturbed by the presence of the mechanism.

As illustrated in FIG. 1, the lens system according to the invention is advantageous since it can be produced in very compact dimensions. Especially, very slim versions are possible, since it is seen that no extra space is required for the pressure release mechanism outside the pathway P. This means that the outer dimensions of the fluid lens container C determines an outer diameter of the lens system. E.g. it is possible to produce cylindrical embodiments with an outer diameter of less than 5 mm, less than 3 mm, and even less than 2 mm.

Figure 2:
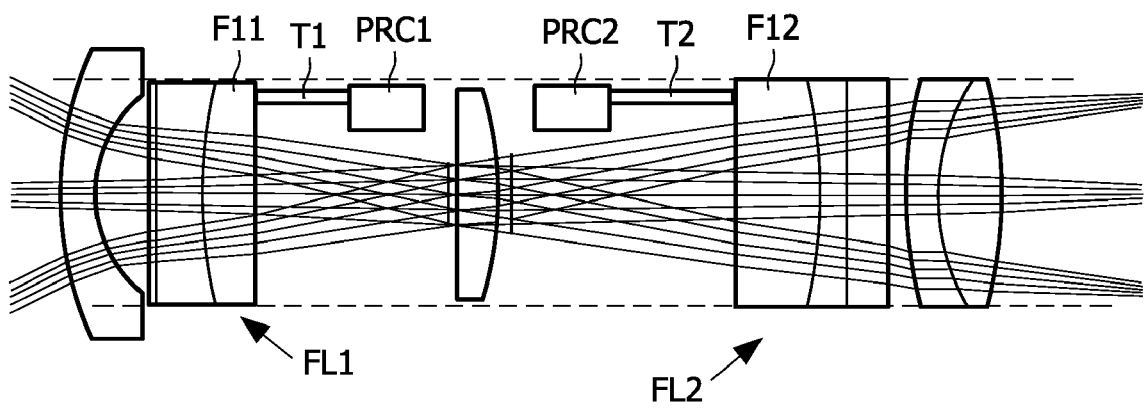
FIG. 2 illustrates a lens embodiment with two fluid lenses each with a pressure release container.

FIG. 2 illustrates a lens system for a medical endoscope. Incoming waves or rather three bunches of beams are illustrated entering the lens system from the left. The three bunches of beams leaving the lens system to the right are then focused on an image sensor (not shown). The lens system includes to fluid lenses FL1, FL2 with their respective pressure release mechanisms in the form of respective pressure release containers PRC1, PRC2 connected to the fluids F11, F12 of the respective fluid lenses FL1, FL2 via respective hollow tubes T1, T2, e.g. having an outer diameter of 0.5 mm. At high temperatures, the fluids F11, F12 will expand and this expansion will cause the fluid F11, F12 to be transported via the tube T1, T2 to the pressure release container PRC1, PRC2. The pressure release containers PRC1, PRC2 function as reservoirs for the fluid F11, F12 when expanded due to high temperatures, thus helping to keep down the pressure inside the fluid lenses FL1, FL2. The containers PRC1, PRC2 can be formed compressible or rigid. In case the containers PRC1, PRC2 are rigid, they may enclose a compressible body to accommodate volume changes.

As seen in FIG. 2 the pressure release containers PRC1, PRC2 are positioned in a peripheral part of the pathway of incoming waves or rays, the pathway being illustrated by dashed lines. Hereby their presence does not degrade performance of the lens system. In the illustrated embodiment both of the pressure release containers PRC1, PRC2 are positioned outside the respective containers of the fluid lenses FL1, FL2. PRC1 is positioned before the container, while PRC2 is positioned after the container, seen in the direction of incoming waves.

Due to the position of the pressure release containers PRC1, PRC2 the outer dimensions of the lens system are not increased compared to the same lens system without any pressure releasing mechanism.

Figure 3A:
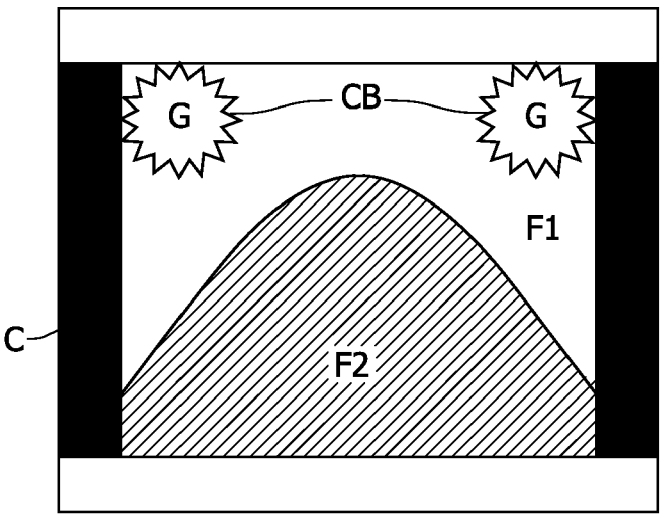
FIGS. 3a and 3b illustrate a pressure release mechanism in the form of a compressible container positioned within the fluid of a fluid lens.
Figure 3B:
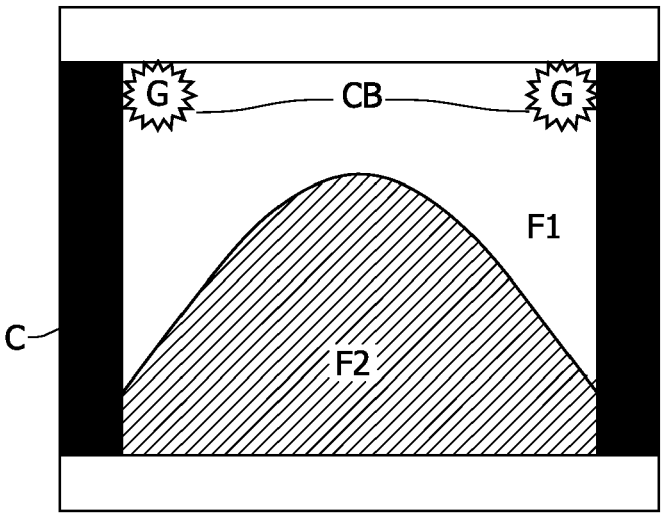

FIGS. 3a and 3b illustrate the same embodiment at two temperatures: FIG. 3a at low temperature, and FIG. 3b at high temperature. In this embodiment the pressure release mechanism is formed by a compressible body CB arranged inside the rigid container C, e.g. cylindrically shaped, and also inside the first fluid F1 which forms a refractive interface with a second fluid F2. The illustrated section illustrates a ring shaped compressible bellows CB, e.g. formed by a metal. The ring shaped bellows CB is gas tight and filled with an easily compressible gas G such as atmospheric air, nitrogen, or $CO_2$. The bellows is positioned towards sidewalls and one end of the container C such that it does not disturb incoming waves in a central pathway.

In FIG. 3a the ring shaped bellows CB is seen to be expanded, since the first fluid F1 has a small volume due to a low temperature. In FIG. 3b the bellows CB is smaller than in FIG. 3a, since the first fluid F1 is now expanded due to a high temperature, and this expansion is absorbed by a corresponding compression of the ring shaped compressible bellows CB.

Figure 4:
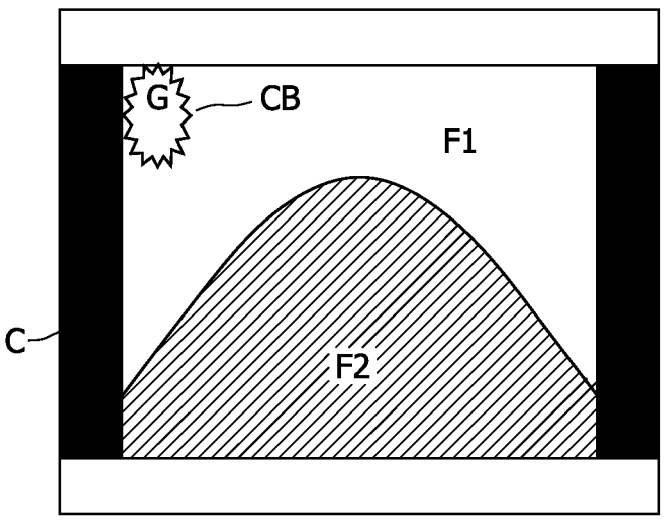
FIG. 4 illustrates another embodiment with a compressible container positioned within the fluid of a fluid lens.

FIG. 4 is a variant of the embodiment of FIGS. 3a and 3b. However, here two separate compressible bodies CB filled with a compressible gas G are positioned inside the first fluid F1. These compressible bodies CB may be formed by small closed metal bellows. It is to be understood, that there may in general be a multiple of such separate compressible bodies CB filled with compressible gas G positioned inside the first fluid F1.

Figure 5:
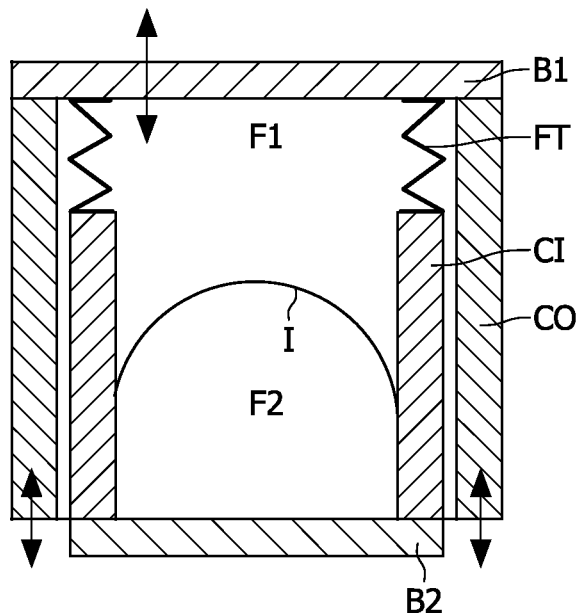
FIG. 5 illustrates an embodiment of the third aspect of the invention.

FIG. 5 illustrates one embodiment of the third aspect of the invention. Two fluids F1, F2 arranged with an interface I for refracting waves, e.g. ultrasonic waves or light, arriving through generally transparent boundaries B1, B2 of the container enclosing the fluids F1, F2. FIG. 5 illustrates a section of the lens system but in preferred embodiments the lens has a cylindrical or frustum shape. Thus, the inner container part CI has a cylindrical wall fixed to the boundary B2, and the outer container part CO has a cylindrical wall fixed to the boundary B1, wherein the outer diameter of the inner wall is only slightly smaller than the inner diameter of the outer wall. Thus, hereby only a minimal clearing is provided to allow a one-dimensional relative translation between the inner and outer container parts CI, CO, as indicated by the double arrows. This is important to ensure that the boundaries B1, B2 do not tilt in relation to each other, which will otherwise compromise the quality of the lens.

A flexible and fluid tight sealing FT, e.g. a rubber or metal bellows shaped sealing, is attached along an upper part of the inner wall and to boundary B1, i.e. to a part moving together with the outer container part CO. Hereby the volume of the first fluid F1 can expand and contract, causing a relative movement between the inner and outer container parts CI, CO.

Figure 6:
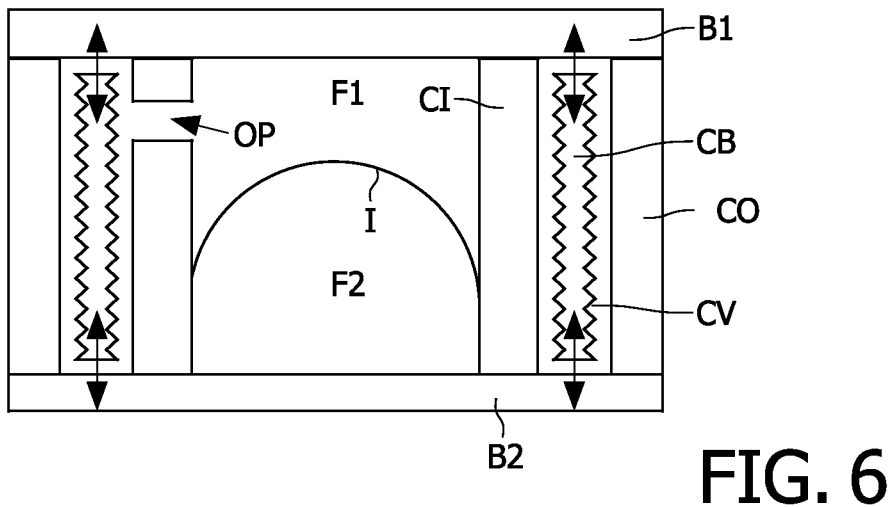
FIG. 6 illustrates another embodiment of the third aspect of the invention.

FIG. 6 illustrates another embodiment of the third aspect of the invention. As in FIG. 5, first and second fluids F1, F2 are arranged with an interface I between them so as to refract waves arriving through generally transparent boundaries B1, B2 of the container enclosing the fluids F1, F2. In this embodiment the inner and outer container parts CI, CO are fixed in relation to each other.

As in FIG. 5, the sketch of FIG. 6 is a section of the lens system which is preferably cylindrical in shape, meaning that both of the inner and outer container parts CI, CO include cylindrical walls. In contrast to the embodiment of FIG. 5, however, the cylindrical inner and outer walls have a substantial different diameter, such that a cavity CV is formed between the inner wall and the outer wall, i.e. preferably a cavity CV surrounding the inner container part CI.

An opening OP in the inner container part connects the first fluid F1 with the cavity CV. Thus, preferably the first fluid F1 fills the cavity CV. In the cavity CV, and thus in direct contact with the first fluid F1, a ring shaped gas filled compressible bellows CB is positioned. The double arrows in connection with the bellows CB indicates its movement upon expansion and contraction of the volume of the first fluid F1. As alternative to one large ring shaped compressible body CB occupying the cavity CV, it is to be understood that several smaller compressible bodies may be positioned. However, to provide a small outer diameter of the lens system, the cavity should be as thin as possible, and thus one bellows CB filling the majority of the cavity CV may be preferred.

The embodiment of FIG. 6 can easily be implemented to have a high mechanical stability since both the inner and outer container parts CI, CO preferably are fixed to the transparent boundaries B1, B2. The opening OP only needs to have a size large enough to allow the first fluid F1 to pass at a speed necessary to transport the first fluid F1 between the main first fluid container and the cavity CV during heating/cooling.

Figure 7:
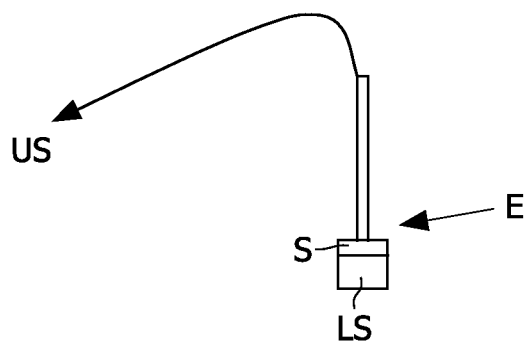
FIG. 7 illustrates a sketch of a medical endoscope according to the invention.

FIG. 7 sketches a medical endoscope E arranged for ultrasonic imaging. A lens system according to the first or third aspect of the invention LS is positioned at a distal end of the endoscope E in connection with an ultrasound sensor S arranged to generate an electric ultrasound signal US in response to the sensed ultrasound signal received through the lens system LS.

To sum up, the invention provides a fluid lens system, e.g. for medical imaging or medical treatment, with a container enclosing a fluid arranged to refract incoming waves. A pressure release mechanism is in contact with the fluid so as to compensate changes in its volume due to thermal variations, e.g. during high temperature medical cleaning. This pressure release mechanism is positioned within a pathway of incoming waves. In preferred embodiments a fluid container connected via a tube to the fluid as a reservoir, is arranged within or outside the container, e.g. beyond an image sensor. Alternatively, an easily compressible body, e.g. a small closed metal bellows enclosing a gas, is positioned inside the fluid to absorb volume changes by compression. In both embodiments, the pressure release elements are preferably positioned in a peripheral part of the pathway of incoming waves to not affect performance of the lens.

In another aspect, a fluid lens includes a container with an inner container part that fits inside an outer container part, wherein the inner container part is in rigid connection to at least a one boundary arranged for penetration of incoming waves. The pressure release mechanism is positioned within the outer container part, and it is in contact with the fluid so as to compensate changes in volume of the fluid due to thermal variations. In one embodiment the inner and outer container parts are arranged for relative one-dimensional movement and fluid tight interconnected. In another embodiment, a fluid filled cavity is formed between the inner and outer container parts, and this cavity houses a compressible body.

The lens systems are suited for applications such as medical endoscopes, catheters and needles, optically as well as acoustically based.

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

Reference signs are included in the claims, however the inclusion of the reference signs is only for clarity reasons and should not be construed as limiting the scope of the claims.

The invention claimed is:

1. A lens system comprising:
    a fluid lens) including a container enclosing a first fluid arranged to refract incoming waves along a pathway of waves passing through the fluid lens, and
    a pressure release mechanism arranged in contact with the first fluid of the fluid lens so as to compensate changes in volume of the first fluid due to thermal variations,
    wherein the pressure release mechanism is positioned within the pathway of the waves passing through the fluid lens.

2. Lens system according to claim 1, wherein the pressure release mechanism is positioned in a peripheral part of the pathway.

3. The lens system according to claim 2, wherein the pressure release mechanism is positioned outside a central part of the pathway so as to avoid affecting refraction properties of the fluid lens.

4. The lens system according to claim 1, wherein the pressure release mechanism is positioned outside the container.

5. The lens system according to claim 1, including a pressure release container connected to the first fluid via a tube so as to accommodate changes in volume of the first fluid due to thermal variations.

6. The lens system according to claim 1, wherein the container is substantially rigid and has two opposing boundaries of a material being substantially transparent for incoming waves.

7. The lens system according to claim 6, wherein the container has a cylindrical shape with the two opposing boundaries defining ends of the container.

8. The lens system according to claim 1, wherein the pressure release mechanism is positioned within a space defined by extension of the sidewalls of the container.

9. The lens system according to claim 1, wherein the fluid lens includes a second fluid different from the first fluid, and wherein the second fluid is arranged with an interface to the first fluid so as to refract incoming waves at the interface.

10. The lens system according to claim 1, wherein the fluid lens is arranged to refract incoming waves being at least one of: light and ultrasonic waves.

11. The lens system according to claim 1, wherein the first fluid is a liquid, such as water or an oil.

12. The lens system according to claim 1, further including a second fluid focus lens including a second pressure release mechanism.

13. A lens system comprising:
    a fluid lens including a container enclosing a first fluid arranged to refract incoming waves;
    a pressure release mechanism arranged in contact with the first fluid of the fluid lens so as to compensate changes in volume of the first fluid due to thermal variations;
    wherein the pressure release mechanism is positioned within a pathway of incoming waves; and
    a sensor arranged to sense waves after refraction in the fluid lens, and wherein the pressure release mechanism is positioned beyond the sensor, seen in a direction of the incoming waves.

14. A lens system comprising:
    a fluid lens including a container enclosing a first fluid arranged to refract incoming waves; and
    a pressure release mechanism arranged in contact with the first fluid of the fluid lens so as to compensate changes in volume of the first fluid due to thermal variations;
    wherein the pressure release mechanism is positioned within a pathway of incoming waves, and
    wherein the pressure release mechanism is positioned inside the container.

15. Lens system according to claim 14, wherein the pressure release mechanism is positioned outside the first fluid.

16. Lens system according to claim 14, wherein the pressure release mechanism is positioned inside the first fluid.

17. The lens system according to claim 16, wherein the pressure release mechanism includes a compressible container enclosing a compressible medium.

18. The lens system according to claim 17, wherein the compressible container includes a bellows enclosing a gas.

19. The lens system according to claim 18, wherein the bellows is a ring shaped bellows positioned in the first fluid in a peripheral part of the pathway of incoming waves.

20. A device including a lens system comprising:
    a fluid lens including a container enclosing a first fluid arranged to refract incoming waves, and
    a pressure release mechanism arranged in contact with the first fluid of the fluid lens so as to compensate changes in volume of the first fluid due to thermal variations,
    wherein the pressure release mechanism is positioned within a pathway of incoming waves; and wherein the device is a medical device.

21. The medical device according to claim 20, wherein the lens system is mounted in connection with one of: a catheter, an endoscope, and a needle.

22. The medical device according to claim 20, wherein the lens system is arranged for one of: medical imaging, and medical treatment.

23. A lens system comprising:
a fluid lens including a container enclosing a first fluid arranged to refract incoming waves along a pathway of waves passing through the fluid lens, the container including an inner container part that fits inside an outer container part, wherein the inner container part is in rigid connection to at least a one boundary arranged for penetration of incoming waves, and
a pressure release mechanism positioned within the outer container part, and arranged in contact with the first fluid of the fluid lens so as to compensate changes in volume of the first fluid due to thermal variations,
wherein the pressure release mechanism includes a flexible connection between the inner and outer container parts arranged to allow pressure release of the first fluid upon relative translation between the inner and outer container parts.

24. A lens system comprising:
a fluid lens including a container enclosing a first fluid arranged to refract incoming waves, the container including an inner container part that fits inside an outer container part, wherein the inner container part is in rigid connection to at least a one boundary arranged for penetration of incoming waves; and
a pressure release mechanism positioned within the outer container part, and arranged in contact with the first fluid of the fluid lens so as to compensate changes in volume of the first fluid due to thermal variations,
wherein the outer container part arranged in rigid connection with a first boundary arranged for penetration of incoming waves, and the inner container part is in rigid connection with a second boundary arranged for penetration of incoming waves, and
wherein the pressure release mechanism includes a flexible and fluid tight connection between the inner and outer container parts arranged to allow pressure release of the first fluid upon relative translation between the inner and outer container parts.

25. Lens system according to claim 24, wherein the inner and outer container parts have cylindrical shapes with different diameters such that the inner container part fits inside the outer container part with a minimal clearing arranged for the relative translation.

26. Lens system according to claim 24, wherein the inner container part further encloses a second fluid arranged with an interface to the first fluid for refraction of incoming waves.

27. A lens system comprising:
a fluid lens including a container enclosing a first fluid arranged to refract incoming waves, the container including an inner container part that fits inside an outer container part, wherein the inner container part is in rigid connection to at least a one boundary arranged for penetration of incoming waves; and
a pressure release mechanism positioned within the outer container part, and arranged in contact with the first fluid of the fluid lens so as to compensate changes in volume of the first fluid due to thermal variations,
wherein the first fluid is connected to a cavity formed between the inner and outer container parts, and
wherein the pressure release mechanism includes a compressible container enclosing a compressible medium arranged in the first fluid inside this cavity so as to release pressure in the first fluid by compression.

28. Lens system according to claim 27, wherein the compressible container is a ring shaped bellows enclosing a gas.

29. Lens system according to claim 27, wherein the inner container part together with the first fluid and a second boundary encloses a second fluid.

* * * * *